United States Patent [19]

Inoue et al.

[11] Patent Number: 4,630,273

[45] Date of Patent: Dec. 16, 1986

[54] LASER DEVICE

[75] Inventors: Hitoshi Inoue, Kanagawa; Norihiro Suenaga, Tokyo; Nobuyuki Suenaga, Kanagawa; Seiji Sugiyama, Kanagawa; Michihiro Kaneda, Kanagawa, all of Japan

[73] Assignee: Nippon Infrared Industries, Co., Ltd., Tokyo, Japan

[21] Appl. No.: 814,157

[22] Filed: Dec. 23, 1985

Related U.S. Application Data

[63] Continuation of Ser. No. 416,062, Sep. 8, 1982, abandoned.

[30] Foreign Application Priority Data

Sep. 11, 1981 [JP]  Japan ................................. 56-143337

[51]  Int. Cl.[4] .............................................. H01S 3/10
[52]  U.S. Cl. .......................................... 372/9; 372/38;
                                                           372/19; 372/33
[58]  Field of Search ................... 372/8, 29, 25, 19, 33,
                                                   372/31, 38, 9; 455/608

[56] References Cited

U.S. PATENT DOCUMENTS

| 3,806,829 | 4/1974 | Duston et al. | 372/25 |
| 4,313,227 | 1/1982 | Eder | 455/608 |
| 4,359,773 | 11/1982 | Swartz et al. | 372/29 |
| 4,429,392 | 1/1984 | Yoshida et al. | 372/29 |
| 4,479,221 | 10/1984 | Kitamura | 372/31 |

OTHER PUBLICATIONS

McMullin; "Leveling the Output of Lasers in a Diode Laser Array", *IBM Tech. Discl. Bulletin*, vol. 19, No. 11, Apr. 1977.

*Primary Examiner*—Léon Scott, Jr.
*Attorney, Agent, or Firm*—Cushman, Darby & Cushman

[57] ABSTRACT

Laser devices being capable of calling freely any desired mode out of a variety of irradiation modes stored beforehead and of reproducing the mode quickly. Specifically, such devices in which a variety of working condition parameters, such as laser output, irradiation time and pulse width, etc., are stored as one set beforehand in a memory within the laser device, and an operator can call a particular mode as the case demands so as to operate the device in a desired state instantly. And further, such devices in which the working condition parameters stored in the said memory can freely be eliminated and changed.

2 Claims, 3 Drawing Figures

LASER DEVICE

This is a continuation of application Ser. No. 416,062 filed Sept. 8, 1982 which was abandoned upon the filing hereof.

BACKGROUND OF THE INVENTION

1. Field of the Invention

The present invention relates to a new structure of laser devices, and particularly to preset type laser devices which are capable of memorizing beforehand laser beam irradiation modes, such as laser output, irradiation time, pulse width and repetitive frequency, and which can freely call any desired irradiation mode.

2. Description of the Prior Art

In using laser devices, users generally adequately change the laser output and irradiation time, and in the case of a pulse laser, pulse width and repetitive frequency, etc., depending on the purpose, use or irradiation object, to start the operation. In other words, the operation is carried out while the irradiation mode of the laser device is set in various ways and changed.

Though the above procedure is naturally applied to laser processings, this is more frequently conducted in laser surgery; as the object is a living body (the human body), a fine and delicate operation is needed, and frequently whenever the situation changes, the irradiation mode of the laser device must be changed.

In changing the irradiation mode, if the number of working condition parameters, such as the laser output, pulse width, irradiation time, etc. as increased, namely if the laser irradiation should be conducted in more delicate and appropriate conditions, the operation will necessarily be more complicated.

Therefore, in the case of laser devices satisfactorily functionable in various ways and designed so as to cope with a variety of operational conditions, a considerably troublesome operation is currently required to operate such devices with an appropriate irradiation mode.

In laser devices for industrial purposes as well as for medical purposes, it is desired to simplify the above-mentioned operation as much as possible and thereby to reduce the operator's burden. Particularly in the field of medical treatments, the necessity of performing a surgical operation very quickly urges strongly development of laser devices for medical purposes in which a variety of irradiation modes can be quickly set by a simple and easy operation.

SUMMARY OF THE INVENTION

This invention is directed to the elimination of the above-mentioned shortcomings of the conventional laser devices. It is therefore an object of the invention to provide preset type laser devices capable of calling freely any desired mode out of a variety of irradiation modes stored beforehand and of reproducing the mode quickly, more specifically such devices in which a variety of working condition parameters, such as laser output, irradiation time and pulse width, etc. are stored as one set beforehand in a memory within the laser device, and an operator can call a particular mode as the case demands so as to operate the device in a desired state instantly, and further such devices in which the working condition parameters stored in the said memory can freely be eliminated and changed.

DETAILED DESCRIPTION OF THE PREFERRED EMBODIMENT

Figure 1:
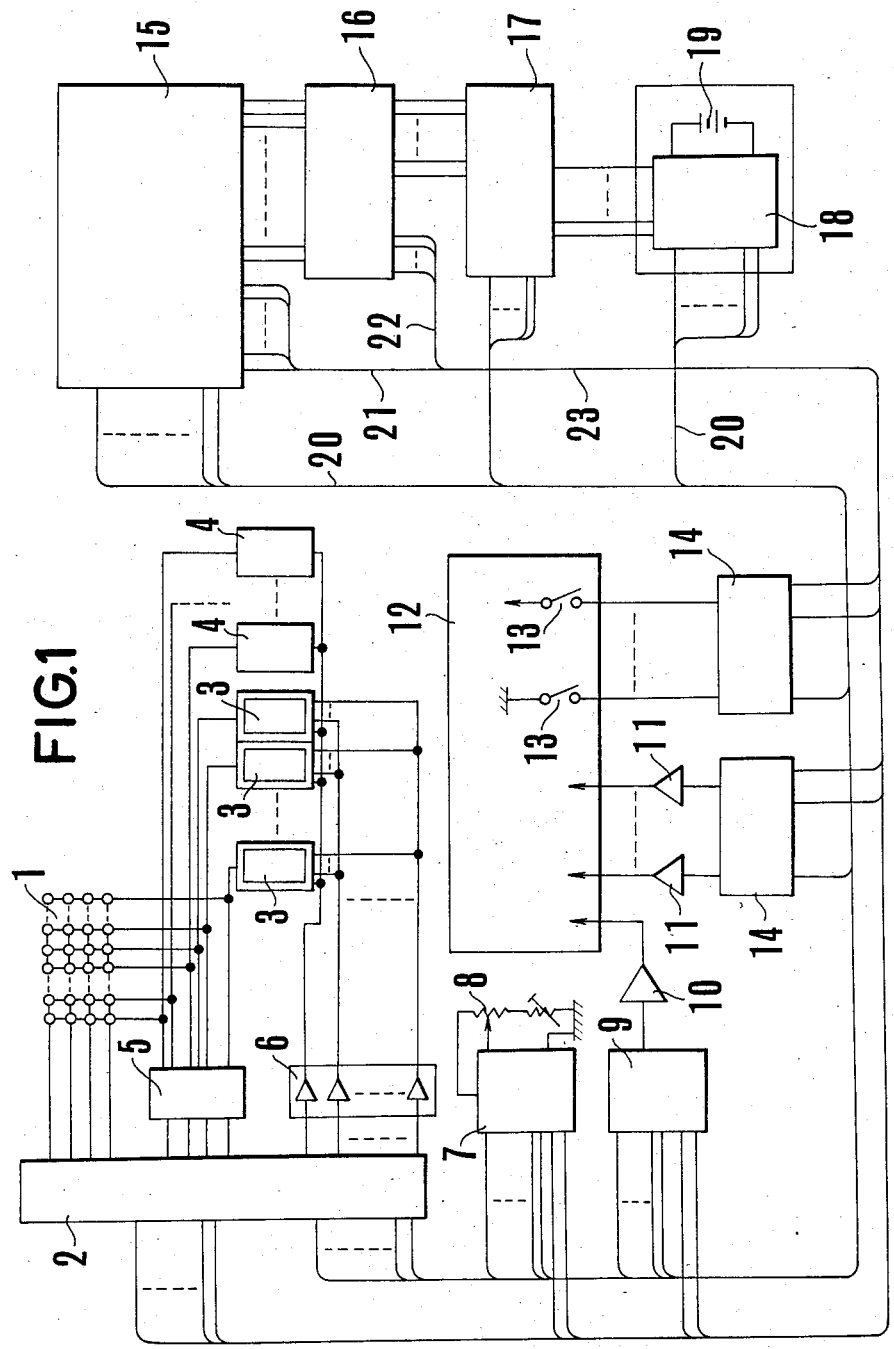
FIG. 1 is a block diagram showing an embodiment of the invention.

An embodiment of the present invention is as shown in the block diagram in FIG. 1. Reference numeral 1 is a switch group consisting of keyboard, switch, digital switch, etc., and a point of intersection of the row and the column represents one switching state; these individual switching states correspond to changeover of the laser oscillation mode (CW oscillation mode or pulse oscillation mode) or mixture of the said two modes, and in the case of pulse beam irradiation, they correspond to setting of pulse width, and then repetition rate, and setting of irradiation number of times, etc. respectively. These plural working condition parameters are incorporated into one set, which forms one irradiation mode. Also, the said switch group 1 corresponds to designation of address on a memory 18 for condition storage as mentioned later, and reading and writing of the said memory.

The switch group 1 is, as the name implies, generally arranged on an operation panel of the device. Through the switch group, the irradiation mode is set and changed.

A variable resistor 8 is used for changing a continuous volume which is inconvenient to set in the switch group 1 such as the keyboard, etc., for instance, for adjustment of laser outputs, etc. Though one piece of the variable resistor is only provided in this embodiment, more than one piece are provided according to demand.

Reference numeral 3 is an indicator displaying the Arabic numerals and 4 is a luminous indicator. These indicators correspond to setting conditions of the switch group and the variable resistor 8, and indicate an operating state of the device. In this way the indicators 3 and 4 display laser oscillation mode, pulse width and repetitive frequency, etc., corresponding to the said switching state.

I/O controller 2 is controlled on a time-sharing base by a signal from CPU15 as described later, and controls signals from the switch group 1, to the indicators 3 and 4. At this time, necessary information is input and output through a data bus 20.

Decoder 5 decodes signals from the I/O controller 2 and said indicators 3 and 4 are lighted.

Buffer amplifier 6 lights the said indicators 3 and 4 by the signal from I/O controller 2.

A/D converter 7 to which the variable resistor 8 is connected encodes D.C. voltage change input from the said resistor 8 into a digital signal corresponding to the voltage value, and outputs to the data bus 20. However, the A/D conversion operation and data fetch are carried out according to an instruction from CPU15 only when they are required by CPU15. In other cases, the data bus of converter 7 is separated by others.

D/A converter 9 fetches the encoding data output from CPU15 from the data bus 20, and outputs a corresponding analogue signal to an analog amplifier 10. At this time, the said converter 9 fetches always the encoding data CPU15 outputs.

The analog amplifier 10 amplifies the output from the D/A converter 9 to a necessary value so as to output into an input/output (I/O) unit of the device 12 as described later. That is, it sets each portion of the device as desired, as described later.

Reference numeral 14 is a buffer for input signals at contacts of individual portions of the device and output signals for control. The buffer 14 is provided with functions to prevent noises from entering CPU15 and, in the case of output signals, to amplify them to a necessary voltage or current value, and also a latch function to hold data. A signal to be output from the buffer 14 is amplified by the buffer amplifier 11 and input to the I/O unit of the device 12.

The I/O unit of the device 12 shows internal points of the device to be controlled, and control of these points determines all operations of the device from starting to stopping. Reference numeral 13 is a sensor signal to detect operational states of the device as shown by the switch.

A CPU main circuit 15 is activated by a program stored in ROM (Read Only Memory) within memory 17 and exchanges data outside by means of a data bus 20, an address bus 22, and an I/O control bus 21, etc., to control all the operations of the device.

A selector 16 has a function to make CPU15 select memories 17, 18 and various I/O portions, and to decode the address data output by CPU15 and to distribute the data respectively.

As aforementioned, the ROM within the memory 17 is a memory to store a program, and all the operations of the device are written in the memory as CPU instructions. In the memory 17, RAM (memory for CPU operation) is also stored and CPU15 uses RAM to store operation and data.

Reference numeral 18 is a memory able to both read and write (hereafter, called condition storage memory) and the various working condition parameters mentioned before are written in this memory. The memory 18 is a volatile C-MOS type memory with less electricity consumption and is backed up with a battery as shown in the figure. A non-volatile RAM can be used instead.

Figure 2:
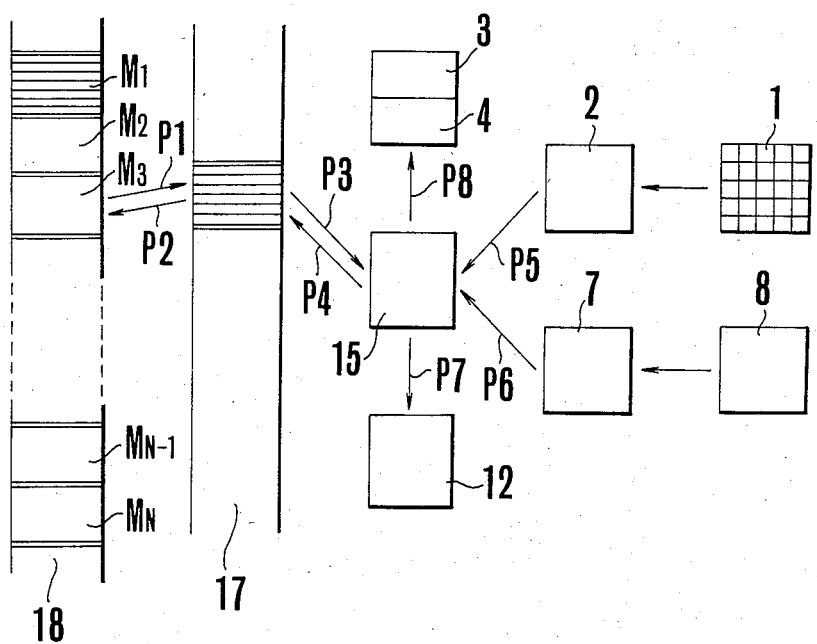
FIG. 2 is a flow chart showing the operation of the embodiment.
Figure 3:
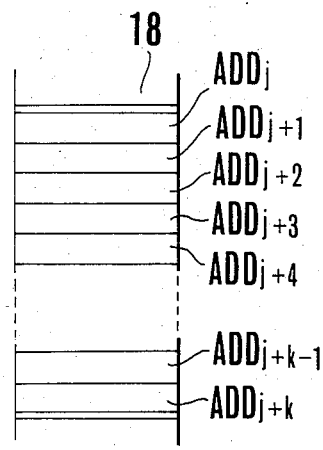
FIG. 3 is a diagram showing data-structure of a working condition storing memory (RAM).

As shown in FIG. 2 and FIG. 3, the condition storage memory 18 is divided into n pieces of regions, $M_1$, $M_2$, ..., $M_n$ and each of these regions are further divided into k pieces of sub-regions to store the irradiation modes. The various working condition parameters mentioned before are stored in these k pieces of sub-regions. Though, not shown in the figure, in the memory 18, condition flags and numerical data encoded in binary are individually set in separate regions and their positions are fixed. A battery 19 is a data storage battery necessary when a volatile memory is used.

Next, referring to the flow chart showing reading and writing of data in FIG. 2, the operation of the laser device according to the present invention will be described.

As above described, the operating state of the device is controlled by the switch group 1 and the variable resistor 8, etc. on the operation panel. The data writing operation is performed as follows. After a signal from the switch group 1 is once input to the I/O controller 2, it is taken as a path P5 in CPU15. Likewise, after a signal from the variable resistor 8 is input to the A/D converter 7, it is taken as a path P6 in CPU15. These signals are transmitted via the data bus 20 and CPU15 judges from these signals which switch of the switch group 1 is in the ON condition.

At this time, CPU15 makes different operations depending upon its judgement, as to which switch of the switch group 1 is in the ON condition. According to the kind of the switch which has been operated, an executive address jumps at an address corresponding to the said switch among the CPU instruction group stored in ROM of the memory 17, and executes the instruction. In case, however, data are represented by the switch, these data fetched in CPU15 are given necessary operation while performing data-exchange with the working RAM of the memory 17, according to the mode determined by the kind of the instruction line switch which has been turned before. After that, these data are again stored in the working RAM. The foregoing operation is shown by a path P4.

With the above operation, symbols and numerals showing the operating state are displayed in the indicators 3 and 4, as shown by a path P8. If setting of the working conditions has been completed, working condition parameters necessary for operation of the device are stored as one set in the working RAM. Therefore, when the working conditions are to be stored, contents of the working RAM are transferred, if an appropriate address on the condition storage memory 18 is designated by the switch group 1 and written as shown by a path P2.

Supposing the address in the memory 18 for the condition storage RAM is j and a number of working condition parameters to be stored is k, a series of parameters consisting of k pieces are stored between j and j+k addresses, as shown in FIG. 3.

If the operation mode consisting of n sets of a wide variety of working condition parameters are successively stored in appropriate addresses of the condition storage memory 18 and thereafter the device is desired to be operated under a particular working condition, the address corresponding to the said working condition can be called. That is, in this case, the content of the condition storage RAM corresponding to the designated address is transferred to the working RAM as shown by a path 1. Then, CPU15 activates the I/O unit of the device 12 according to the content of the working RAM17 so as to control the working state of the device to operate with a desired irradiation mode. The foregoings are shown by the path P3 and path P7.

Meanwhile, data which are once written in the condition storage RAM of the memory 18 can be changed over and over again, since the memory is of the RAM type.

As described in detail so far, according to the present invention, a particular irradiation mode as desired can be freely called out of a variety of irradiation modes stored beforehand and can be reproduced very quickly. Thus, this eliminates a complicated operation for irradiation condition setting for an operator, and provides an appropriate device useful both for medical purposes and for industrial purposes. In addition, a desired irradiation mode can be accurately reproduced, thus eliminating any possibility of conducting improper irradiation to an irradiation object.

Accordingly, the present invention contributes to improved safety in the medical treatment field and increased productivity in the industrial field.

As will be obvious to those skilled in the art, numerous variations and modifications may be made in the abovedescribed device without departing from the spirit and scope of the invention. For instance, the device of the present invention may be applied to electric surgery as well as laser surgery.

In this case, the working condition parameters mentioned before should include those for an electric surgery mode, a cutting mode, a coagulation mode or a mixture of the foregoing two modes as well as for setting of electric surgery outputs.

What we claim:

1. A medical laser device having a control system for controlling the laser device to emit a desired laser irradiation for a medical treatment, said control system comprising:

a group of switches each of which when actuated represent individual operational parameters of a pulse ocsillation mode, presetting of the individual operational parameters forms an irradiation mode which includes, laser output, irrdiation time, pulse length and repetition period;

means for converting the preset individual operational condition parameters input through said actuated switches into an electrical signal and for converting said electrical signal to a designation of an address in a memory;

said memory stores at different addresses, combinations of said individual operational condition parameters, said stored combinations defining different specific laser irradiation modes; and control means for retrieving from said memory a specific laser irradiation mode, corresponding to the address provided by said converting means, and for generating a control signal for driving the laser device in response to said individual operational condition parameters defining the specific laser irradiation mode.

2. A laser according to claim 1, which further comprises means for setting the individual operational condition parameters to a continuous value, and means for converting the continuous value into an electrical signal.

* * * * *